United States Patent
Freeman et al.

(10) Patent No.: US 7,333,211 B2
(45) Date of Patent: Feb. 19, 2008

(54) METHOD FOR DETERMINING A QUALITATIVE CHARACTERISTIC OF AN INTERFEROMETRIC COMPONENT

(75) Inventors: Neville John Freeman, Utkinton (GB); Graham Cross, Stockton-on-Tees (GB); Gerard Anthony Ronan, Salford (GB)

(73) Assignee: Farfield Sensors Limited, Wythenshawe, Manchester (GB)

( * ) Notice: Subject to any disclaimer, the term of this patent is extended or adjusted under 35 U.S.C. 154(b) by 399 days.

(21) Appl. No.: 10/505,917

(22) PCT Filed: Mar. 14, 2003

(86) PCT No.: PCT/GB03/01091

§ 371 (c)(1),
(2), (4) Date: Aug. 27, 2004

(87) PCT Pub. No.: WO03/078984

PCT Pub. Date: Sep. 25, 2003

(65) Prior Publication Data

US 2005/0163413 A1    Jul. 28, 2005

(30) Foreign Application Priority Data

Mar. 14, 2002  (GB) .................................. 0206010.1
Mar. 27, 2002  (GB) .................................. 0207167.8

(51) Int. Cl.
- G01B 9/02   (2006.01)
- G02B 6/00   (2006.01)
- B32B 5/02   (2006.01)
- B32B 27/04  (2006.01)
- B32B 27/12  (2006.01)
- G01N 21/00  (2006.01)

(52) U.S. Cl. .................... 356/481; 385/12; 422/82.11

(58) Field of Classification Search ............... 356/477, 356/481; 385/12; 250/227.19, 227.27; 436/167, 436/169, 171; 422/82.11
See application file for complete search history.

(56) References Cited

U.S. PATENT DOCUMENTS

| | | | |
|---|---|---|---|
| 4,950,074 A * | 8/1990 | Fabricius et al. ........... 356/133 |
| 5,120,131 A | 6/1992 | Lukosz | |
| 5,173,747 A * | 12/1992 | Boiarski et al. ............ 356/481 |
| 5,262,842 A | 11/1993 | Gauglitz et al. | |
| 5,377,008 A * | 12/1994 | Ridgway et al. ............ 356/481 |
| 5,465,151 A * | 11/1995 | Wybourne et al. .......... 356/481 |
| 6,130,439 A | 10/2000 | Le Menn | |
| 6,330,064 B1 * | 12/2001 | Rieder ........................ 356/481 |
| 6,335,793 B1 * | 1/2002 | Freeman et al. ............ 356/477 |
| 6,429,023 B1 * | 8/2002 | Gharavi ...................... 436/167 |
| 6,483,959 B1 * | 11/2002 | Singh et al. .................. 385/12 |
| 7,050,176 B1 * | 5/2006 | Cross et al. ................. 356/517 |
| 7,062,110 B2 * | 6/2006 | Freeman et al. .............. 385/12 |
| 2004/0004180 A1 * | 1/2004 | Freeman et al. ....... 250/227.14 |
| 2004/0008919 A1 * | 1/2004 | Freeman et al. .............. 385/12 |
| 2004/0245475 A1 * | 12/2004 | Jones et al. ................. 250/391 |
| 2005/0009196 A1 * | 1/2005 | Freeman et al. ............ 436/149 |
| 2005/0163413 A1 * | 7/2005 | Freeman et al. .............. 385/12 |
| 2005/0254744 A1 * | 11/2005 | Freeman ...................... 385/12 |

FOREIGN PATENT DOCUMENTS

WO    WO 9822807    5/1998

* cited by examiner

Primary Examiner—Patrick Connolly
(74) Attorney, Agent, or Firm—Fay Sharpe LLP

(57) ABSTRACT

The present invention relates to a method for determining a qualitative characteristic of an interferometric component (eg a planar waveguide structure) or a process for determining a qualitative characteristic of a stimulus of interest to which the interferometric component (eg the planar waveguide structure) has been exposed by measuring a non-positional characteristic of the interference fringes.

7 Claims, 7 Drawing Sheets

Distance

Light Intensity $$\text{Quality} = \sum_{1}^{P} |\text{Observed-Calculated}|_{i}^{i}$$

METHOD FOR DETERMINING A QUALITATIVE CHARACTERISTIC OF AN INTERFEROMETRIC COMPONENT

BACKGROUND

The present invention relates to a method for determining a qualitative characteristic of an interferometric component (eg a planar waveguide structure) or a process for determining a qualitative characteristic of a stimulus of interest to which the interferometric component (eg the planar waveguide structure) has been exposed.

Generally speaking, it is known to make use of the evanescent field component of electromagnetic radiation incident on a planar waveguide structure (ie the field which extends outside the guiding region) to sense discrete changes in optical properties (see inter alia GB-A-2228082, U.S. Pat. No. 5,262,842, WO-A-97/12225 and GB-A-2307741). This technique relies on "leakage" of optical signals from a planar waveguide into a sensing layer typically formed from an absorbent polymer.

Based on the principles of interferometry, the use of a planar waveguide structure to quantify (ie to detect the amount of (eg concentration of) or changes in) a stimulus of interest is disclosed in inter alia WO-A-98/22807 and WO-A-01/36945. Such planar waveguide structures comprise a planar sensing waveguide or sensing layer and generate a plurality of interference fringes in an interference pattern. Positional measurements such as the movement of the interference fringes in response to the exposure of the planar waveguide structure to the stimulus of interest may be made to quantify the stimulus of interest. However such positional information is subject to limitations. The evanescent component of the optical signal being guided by the planar waveguide, is typically small (leading to limited interrogation of the sensing layer). Moreover the evanescent component varies exponentially and may extend beyond the sensing layer. This means that the aggregate response of the planar waveguide structure is non-linear being dependent on factors contributing to the change in the effective refractive index of the planar waveguide structure ie factors such as changes in dimension (eg physical thickness) of the sensing layer and/or changes in composition (ie intrinsic refractive index) of the sensing layer and beyond.

WO-A-01/36946 (Farfield Sensors Limited) discloses the use of TE and TM polarisations to differentiate factors (eg dimensional and compositional factors) contributing to changes in the effective refractive index of a planar waveguide structure. The response of the two polarisations are solved for consistency with a simple mono-adlayer model. However this method is limited by factors such as non-uniformity, optical activity or unknown composition of the sensing layer.

BRIEF SUMMARY

The present invention is based on the recognition that certain characteristics of the output of (eg the interference fringes generated by) an interferometric component such as a planar waveguide structure may be related to qualitative characteristics of the interferometric component or to qualitative characteristics of a stimulus of interest to which it has been exposed. More particularly, the present invention relates to a method or process for determining a qualitative characteristic of a planar waveguide structure or of a stimulus of interest to which it has been exposed by exploiting a non-positional measurement of the interference fringes.

Thus viewed from one aspect the present invention provides a method for determining a qualitative characteristic of an interferometric component comprising:
(A) irradiating the interferometric component with electromagnetic radiation to generate interference fringes;
(B) measuring a non-positional characteristic of the interference fringes; and
(C) relating the non-positional characteristic of the interference fringes to the qualitative characteristic of the interferometric component.

The interferometric component may be a waveguide (eg a slab or channel waveguide) or a fibre optic component.

Preferably the interferometric component is a planar waveguide structure including:

either (a) one or more sensing layers capable of inducing in a planar secondary waveguide a measurable response to a change in the localised environment caused by the introduction of or changes in the stimulus of interest and a planar inactive (eg deactivated) secondary waveguide in which the sensing layer is incapable of inducing a measurable response to a change in the localised environment caused by the introduction of or changes in the stimulus of interest or (b) a planar sensing waveguide capable of exhibiting a measurable response to a change in the localised environment caused by the introduction of or changes in the stimulus of interest and a planar inactive (eg deactivated) waveguide substantially incapable of exhibiting a measurable response to a change in the localised environment caused by the introduction of or changes in the stimulus of interest, wherein the method comprises:
(A) irradiating the planar waveguide structure with electromagnetic radiation to generate interference fringes;
(B) measuring a non-positional characteristic of the interference fringes; and
(C) relating the non-positional characteristic of the interference fringes to the qualitative characteristic of the planar waveguide structure.

Preferably each planar waveguide permits propagation of electromagnetic radiation in any arbitrary direction within the plane and may for example be a slab waveguide.

Interference fringes are generated when the electromagnetic radiation is coupled into free space. The pattern of interference fringes and the non-positional characteristic of the interference fringes may be measured by a conventional measuring means (see for example WO-A-98/22807) eg one or more detectors which measure the intensity of electromagnetic radiation. The one or more detectors may comprise one or more photodetectors. Where more than one photodetector is used these may be arranged in an array.

In a preferred embodiment of the method, the non-positional characteristic of the interference fringes is the fringe period. For a planar waveguide structure, the fringe period (P) of the interference fringes is determined by the following equation:

$$P = \frac{\lambda Z}{d}$$

(where:
d is the separation of the two planar waveguides (ie either the separation of the planar secondary waveguide and planar inactive secondary waveguide or the separation of the planar sensing waveguide and planar inactive waveguide), z is the distance from the detector to the two planar waveguides (ie either to the planar secondary waveguide and planar inactive secondary waveguide or to the planar sensing waveguide and planar inactive waveguide), and $\lambda$ is the wavelength of the electromagnetic radiation).

In this embodiment, the qualitative characteristic may be the status of the interferometric component. For a planar waveguide structure, given that $\lambda$, Z and d are known, step (C) of the method may further comprise:

(C1) calculating P;

(C2) comparing P calculated in step (C1) with the fringe period measured in step (B); and (C3) relating the results of the comparison of step (C2) to the status of the planar waveguide structure.

Steps (C1) to (C3) may be advantageously performed at start up. If the results of the comparison of step (C2) are outside specified parameters, the interferometric component may be unsuitable or failed.

In this embodiment, the qualitative characteristic may be the planar waveguide separation. The separation d of the two planar waveguides (ie either the separation of the planar secondary waveguide and planar inactive secondary waveguide or the separation of the planar sensing waveguide and planar inactive waveguide) may vary according to the manufacturing parameters and so not necessarily be known to a user. By permitting d to be determined (eg prior to use), the method of the invention allows a planar waveguide structure to be effectively 'optically bar coded'.

In this embodiment, the qualitative characteristic may be the wavelength of the electromagnetic radiation. An interferometric component may be excited with electromagnetic radiation of any wavelength $\lambda$. Measurement of the fringe period in accordance with the method of the invention permits the wavelength of the electromagnetic radiation to be determined straightforwardly (eg without opening the housing). In turn, this information could be used to verify the correct operation of the source of electromagnetic radiation.

In a preferred embodiment of the method, the non-positional characteristic of the interference fringes is the shape of the fringe envelope. In this embodiment, the qualitative characteristic may be the attitude of the planar waveguide structure relative to the measuring means (eg detector). The qualitative characteristic may be the angular alignment of the planar waveguide structure relative to the measuring means. For example, a distortion in the fringe envelope may be related to angular misalignment of the planar waveguide structure relative to the measuring means.

In a preferred embodiment of the method, the non-positional characteristic of the interference fringes is the position of the fringe envelope. In this embodiment, the qualitative characteristic may be the lateral alignment of the planar waveguide structure relative to the measuring means (eg detector). For example, a re-positioning of the fringe envelope may be related to lateral misalignment of the planar waveguide structure relative to the measuring means.

In a preferred embodiment of the method, the non-positional characteristic of the interference fringes is the contrast of the interference fringes (eg the difference in intensity between the outer fringe envelope and the inner fringe envelope). For example, the contrast may be the difference in intensity between the outer fringe envelope and the inner fringe envelope at a corresponding position in the pattern. Preferably the contrast may be the difference in intensity between the maxima of the outer fringe envelope and the maxima of the inner fringe envelope. The qualitative characteristic may be the scattering loss from the interferometric component. For example, scattering losses may be caused by diffraction processes.

In a preferred embodiment of the method, the non-positional characteristic of the interference fringes is the integral under the fringes. In this embodiment, the qualitative characteristic may be the power of the electromagnetic radiation passing through the interferometric component (eg through the planar waveguide structure ie the total power of electromagnetic radiation in either the planar sensing waveguide and planar inactive waveguide or the planar secondary waveguide and planar inactive secondary waveguide).

In a preferred embodiment of the method, the non-positional characteristic of the interference fringes is the interference pattern (ie as a whole). In this embodiment, for a planar waveguide structure the qualitative characteristic may be the status of the planar waveguide structure. Given that $\lambda$, Z, d (as defined hereinbefore) and the dimensions of the planar waveguide structure are known, step (C) of the method may further comprise:

(C1) calculating an ideal interference pattern;

(C2) comparing the ideal interference pattern calculated in step (C1) with the interference pattern measured in step (B); and (C3) relating the results of the comparison of step (C2) to the status of the planar waveguide structure.

Steps (C1) to (C3) may be advantageously performed at start up. For example, the status of the planar waveguide structure may indicate an optical aberration or may indicate a subset of interference fringes which are most suitable for subsequent use.

Viewed from a further aspect the present invention provides a process for determining a qualitative characteristic of a stimulus of interest (eg a chemical, physical or biological stimulus of interest) in a localised environment, said process comprising:

(A) providing an interferometric component capable of exhibiting a measurable response to a change in the localised environment caused by the introduction of or changes in the stimulus of interest;

(B) introducing the stimulus of interest into the localised environment;

(C) irradiating the interferometric component with electromagnetic radiation to generate interference fringes;

(D) measuring a non-positional characteristic of the interference fringes; and (E) relating the non-positional characteristic of the interference fringes to the qualitative characteristic of the stimulus of interest.

The interferometric component may be a waveguide (eg a slab or channel waveguide) or a fibre optic component.

Preferably the interferometric component is a planar waveguide structure including:

either (a) one or more sensing layers capable of inducing in a planar secondary waveguide a measurable response to a change in the localised environment caused by the introduction of or changes in the stimulus of interest and a planar inactive (eg deactivated) secondary waveguide in which the sensing layer is incapable of inducing a measurable response to a change in the localised environment caused by the introduction of or changes in the stimulus of interest or (b) a planar sensing waveguide capable of exhibiting a measurable response to a change in the localised environment caused by the introduction of or changes in the stimulus of interest and a planar inactive (eg deactivated) waveguide substantially incapable of exhibiting a measurable response to a change in the localised environment caused by the introduction of or changes in the stimulus of interest.

The non-positional characteristic of the interference fringes (step (D)) may be measured by a conventional measuring means (see for example WO-A-98/22807) eg one or more detectors which measure the intensity of electromagnetic radiation.

In a preferred embodiment, step (A) of the process of the invention further comprises:

(A') irradiating the interferometric component with electromagnetic radiation to generate first interference fringes;

(A") measuring a non-positional characteristic of the first interference fringes, and steps (C), (D) and (E) comprise:

(C) irradiating the interferometric component with electromagnetic radiation to generate second interference fringes;

(D) measuring a non-positional characteristic of the second interference fringes; and (E) relating the non-positional characteristic of the first and second interference fringes to the qualitative characteristic of the stimulus of interest.

Steps (A), (A') and (A") may be performed at start-up. The results may be stored electronically (eg as calibration data).

In a preferred embodiment of the process, the non-positional characteristic of the interference fringes is the contrast of the fringes (eg the difference in intensity between the outer fringe envelope and the inner fringe envelope). For example, the contrast may be the difference in intensity between the outer fringe envelope and the inner fringe envelope at a corresponding position in the pattern. Preferably the contrast may be the difference in intensity between the maxima of the outer fringe envelope and the maxima of the inner fringe envelope.

In this embodiment, the qualitative characteristic may be the degree of non-random deposition (eg nucleation) of the stimulus of interest. Preferably the degree of nucleation may be quantified.

In this embodiment, the qualitative characteristic may be the degree of absorbtion of electromagnetic radiation by the stimulus of interest, for example the degree of absorbtion of electromagnetic radiation by a chromophore or fluorophore. All stimuli have a real and imaginary component of refractive index and in accordance with the preferred embodiment of the process of the invention, the qualitative characteristic may be the imaginary component of the refractive index. The imaginary component of the refractive index is a fundamental characteristic of the stimulus of interest. Further in accordance with the preferred embodiment of the process of the invention, the qualitative characteristic may be the extinction coefficient of the stimulus of interest (eg chromophore or fluorophore).

In a preferred embodiment of the process of the invention, steps (C), (D) and (E) comprise:

(C1) irradiating the interferometric component with electromagnetic radiation in TE mode to generate first interference fringes;

(C2) irradiating the interferometric component with electromagnetic radiation in TM mode to generate second interference fringes;

(D1) measuring a non-positional characteristic of the first interference fringes;

(D2) measuring a non-positional characteristic of the second interference fringes; and (E) relating the non-positional characteristic of the first interference fringes and the non-positional characteristic of the second interference fringes to the qualitative characteristic of the stimulus of interest.

Particularly preferably step (A) of this embodiment further comprises:

(A1) irradiating the interferometric component with electromagnetic radiation in TE mode to generate first interference fringes;

(A2) irradiating the interferometric component with electromagnetic radiation in TM mode to generate second interference fringes;

(A3) measuring a non-positional characteristic of the first interference fringes;

(A4) measuring a non-positional characteristic of the second interference fringes;

and steps (C1), (C2), (D1), (D2) and (E) comprise:

(C1) irradiating the interferometric component with electromagnetic radiation in TE mode to generate third interference fringes;

(C2) irradiating the interferometric component with electromagnetic radiation in TM mode to generate fourth interference fringes;

(D1) measuring a non-positional characteristic of the third interference fringes;

(D2) measuring a non-positional characteristic of the fourth interference fringes;

(E) relating the non-positional characteristic of the first, second, third and fourth interference fringes to the qualitative characteristic of the stimulus of interest.

First and second irradiating means may be adapted to perform A1/C1 and A2/C2 sequentially or simultaneously. The first and second irradiating means may comprise the same or different electromagnetic radiation sources. Where different sources are used, an optical switch (eg a rotating mirror) may be used to switch rapidly between the two. Alternatively, a single electromagnetic radiation source may be used to simultaneously excite TE and TM modes of the planar waveguide structure by aligning the polarisation vector of a linearly polarised source at an angle (eg an angle of 45°) with respect to the plane of the planar sensing waveguide or sensing layer. An active analyser system may be used to alternately remove the unwanted TE or TM mode radiation during data capture of the desired TM or TE output radiation respectively. The active analyser system may comprise an electro-optic half wave plate placed in series with an analyser. In a preferred embodiment, an adjustable analyser may be used to measure first and second (and third and fourth) interference fringes separately. The measurements may be synchronised with the excitation and/or polarisation procedure to ensure correlation with TE and TM excitation. A controller may be provided to synchronise the one or more electromagnetic radiation sources and one or more detectors. For example, the controller may capture the data from a photodetector (eg photodiode) array. The firing of the (or each) electromagnetic radiation source may be synchronised by the controller with the alternate capture of the interference fringes generated in TM mode and TE mode.

Particularly preferably in this embodiment, the non-positional characteristic of the interference fringes is the fringe contrast.

In this embodiment, the qualitative characteristic may be the distance between the stimulus of interest (eg a chromophore or fluorophore) and the interferometric component (eg the planar waveguide structure). Generally this is proportional to the relative change in fringe contrast between TE and TM mode electromagnetic radiation following exposure to the stimulus of interest.

In this embodiment, the qualitative characteristic may be the degree of anisotropy of the stimulus of interest.

In this embodiment, the qualitative characteristic may be magnetic properties of the stimulus of interest. For example, the magnetic properties may be the presence of a permanent magnetic moment.

In this embodiment, the qualitative characteristic may be optical activity of the stimulus of interest. Optical activity may cause transfer of energy from one polarisation to the other (TE to TM or vice versa).

In a preferred embodiment of the process of the invention, steps (C), (D) and (E) comprise:

(C1) irradiating the interferometric component with electromagnetic radiation in a first order mode to generate first interference fringes;

(C2) irradiating the interferometric component with electromagnetic radiation in a second order mode to generate second interference fringes;

(D1) measuring a non-positional characteristic of the first interference fringes;

(D2) measuring a non-positional characteristic of the second interference fringes; and (E) relating the non-positional characteristic of the first interference fringes and the non-positional characteristic of the second interference fringes to the qualitative characteristic of the stimulus of interest.

The first order mode and second order mode are different. For example, the first order mode may be the fundamental mode and the second order mode may be a higher (second, third or $n^{th}$) order mode. Steps (C1) and (C2) may be carried out simultaneously or sequentially. Particularly preferably step (A) of this embodiment further comprises:
  (A1) irradiating the interferometric component with electromagnetic radiation in the first order mode to generate first interference fringes;
  (A2) irradiating the interferometric component with electromagnetic radiation in the second order mode to generate second interference fringes;
  (A3) measuring a non-positional characteristic of the first interference fringes;
  (A4) measuring a non-positional characteristic of the second interference fringes;

and steps (C1), (C2), (D1), (D2) and (E) comprise:
  (C1) irradiating the interferometric component with electromagnetic radiation in the first order mode to generate third interference fringes;
  (C2) irradiating the interferometric component with electromagnetic radiation in the second order mode to generate fourth interference fringes;
  (D1) measuring a non-positional characteristic of the third interference fringes;
  (D2) measuring a non-positional characteristic of the fourth interference fringes;
  (E) relating the non-positional characteristic of the first, second, third and fourth interference fringes to the qualitative characteristic of the stimulus of interest.

Particularly preferably in this embodiment, the non-positional characteristic of the interference fringes is the amplitude.

In this embodiment, the qualitative characteristic may be the degree of anisotropy of the stimulus of interest.

In this embodiment, the qualitative characteristic may be magnetic properties of the stimulus of interest. For example, the magnetic properties may be the presence of a permanent magnetic moment.

In this embodiment, the qualitative characteristic may be optical activity of the stimulus of interest. Optical activity may cause energy to be differentially dissipated from the first and second order modes of electromagnetic radiation.

In a preferred embodiment of the process of the invention, steps (C), (D) and (E) comprise:

(C1) irradiating the interferometric component with electromagnetic radiation of a first wavelength to generate first interference fringes;

(C2) irradiating the interferometric component with electromagnetic radiation of a second wavelength to generate second interference fringes;

(D1) measuring a non-positional characteristic of the first interference fringes;

(D2) measuring a non-positional characteristic of the second interference fringes; and (E) relating the non-positional characteristic of the first interference fringes and the non-positional characteristic of the second interference fringes to the qualitative characteristic of the stimulus of interest.

The first and second wavelengths are different. Steps (C1) and (C2) may be carried out simultaneously or sequentially. Particularly preferably step (A) of this embodiment further comprises:
  (A1) irradiating the interferometric component with electromagnetic radiation of the first wavelength to generate first interference fringes;
  (A2) irradiating the interferometric component with electromagnetic radiation of the second wavelength to generate second interference fringes;
  (A3) measuring a non-positional characteristic of the first interference fringes;
  (A4) measuring a non-positional characteristic of the second interference fringes;

and steps (C1), (C2), (D1), (D2) and (E) comprise:
  (C1) irradiating the interferometric component with electromagnetic radiation of the first wavelength to generate third interference fringes;
  (C2) irradiating the interferometric component with electromagnetic radiation of the second wavelength to generate fourth interference fringes;
  (D1) measuring a non-positional characteristic of the third interference fringes;
  (D2) measuring a non-positional characteristic of the fourth interference fringes;
  (E) relating the non-positional characteristic of the first, second, third and fourth interference fringes to the qualitative characteristic of the stimulus of interest.

Particularly preferably in this embodiment, the non-positional characteristic of the interference fringes is the amplitude.

The present invention also relates to a method for determining a qualitative characteristic of a stimulus of interest to which an interferometric component (eg a planar waveguide structure) has been exposed by exploiting a non-positional measurement of the output electromagnetic radiation.

Viewed from a yet further aspect the present invention provides a method for determining a qualitative characteristic of a stimulus of interest (eg a chemical, physical or biological stimulus of interest) in a localised environment, said method comprising:

(A) providing an interferometric component capable of exhibiting a measurable response to a change in the localised environment caused by the introduction of or changes in the stimulus of interest;

(B) introducing the stimulus of interest into the localised environment;

(C) irradiating the interferometric component with electromagnetic radiation in TE and TM mode to generate output electromagnetic radiation;

(D) measuring a transfer of power between TE and TM modes; and (E) relating the transfer of power between TE and TM modes to the qualitative characteristic of the stimulus of interest.

The interferometric component may be a waveguide (eg a slab or channel waveguide) or a fibre optic component.

Preferably the interferometric component is a planar waveguide structure including:

either (a) one or more sensing layers capable of inducing in a planar secondary waveguide a measurable response to a change in the localised environment caused by the introduction of or changes in the stimulus of interest and a planar inactive (eg deactivated) secondary waveguide in which the sensing layer is incapable of inducing a measurable response to a change in the localised environment caused by the introduction of or changes in the stimulus of interest or (b) a planar sensing waveguide capable of exhibiting a measurable response to a change in the localised environment caused by the introduction of or changes in the stimulus of interest and a planar inactive (eg deactivated) waveguide substantially incapable of exhibiting a measurable response to a change in the localised environment caused by the introduction of or changes in the stimulus of interest.

Preferably the qualitative characteristic is the degree of anisotropy of the stimulus of interest.

Step (D) may be carried out using a cross polariser.

Preferably the planar waveguide structure is adapted so as to be usable in evanescent mode or whole waveguide mode.

Thus in a first embodiment of the preferred methods or process of the invention, the planar waveguide structure includes one or more sensing layers capable of inducing in a planar secondary waveguide a measurable response to a change in the localised environment caused by the introduction of or changes in the stimulus of interest.

In this first embodiment, the planar waveguide structure is advantageously adapted to optimise the evanescent component so as to induce in the planar secondary waveguide a measurable response.

In a preferred embodiment, the sensing layer comprises an absorbent material (eg a polymeric material such as polymethylmethacrylate, polysiloxane, poly-4-vinylpyridine) or a bioactive material (eg containing antibodies, enzymes, DNA fragments, functional proteins or whole cells). The absorbent material may be capable of absorbing a gas, a liquid or a vapour analyte containing a chemical stimulus of interest. The bioactive material may be appropriate for liquid or gas phase biosensing. For example, the sensing layer may comprise a porous silicon material optionally biofunctionalised with antibodies, enzymes, DNA fragments, functional proteins or whole cells.

In a preferred embodiment, the planar secondary waveguide comprises silicon oxynitride or silicon nitride. The planar inactive secondary waveguide is capable of acting as a reference layer. It is preferred that the planar secondary waveguide and planar inactive secondary waveguide have identical properties with the exception of the response to the change in the localised environment caused by the introduction of or changes in the stimulus of interest. By way of example, the planar secondary waveguide and planar inactive secondary waveguide is made of silicon oxynitride.

In a second embodiment of the invention, the planar waveguide structure includes a planar sensing waveguide capable of exhibiting a measurable response to a change in the localised environment caused by the introduction of or changes in the stimulus of interest.

In this second embodiment, the planar waveguide structure is adapted to minimise the evanescent component and may be used advantageously in a whole waveguide mode.

In a preferred embodiment, the planar sensing waveguide comprises an absorbent material (eg a polymeric material such as polymethylmethacrylate, polysiloxane, poly-4-vinylpyridine) or a bioactive material (eg containing antibodies, enzymes, DNA fragments, functional proteins or whole cells). The absorbent material may be capable of absorbing a gas, a liquid or a vapour analyte containing a chemical stimulus of interest. The bioactive material may be appropriate for liquid or gas phase biosensing. For example, the planar sensing waveguide may comprise a porous silicon material optionally biofunctionalised with antibodies, enzymes, DNA fragments, functional proteins or whole cells.

Where the planar waveguide structure comprises a planar sensing waveguide adapted for use in whole waveguide mode, an absorbent layer in the form of an overcoating may be present for use as a membrane (for example) to separate out stimuli of interest.

The planar inactive waveguide is capable of acting as a reference layer. The physical, biological and chemical properties of the planar sensing waveguide and planar inactive waveguide are as similar as possible (with the exception of the response to the change in the localised environment caused by the introduction of or changes in the stimulus of interest). Typically the planar inactive waveguide is made of silicon oxynitride.

Preferably the planar waveguide structure constitutes a multi-layered planar waveguide structure (eg a laminated planar waveguide structure). Typically the planar waveguide structure is a multilayered structure of thickness in the range 0.2-10 microns. In a preferred embodiment, each of the plurality of layers in the multi-layered planar waveguide structure are built onto a substrate (eg of silicon) through known processes such as PECVD and LPCVD. Intermediate transparent layers may be added (eg silicon dioxide) if desired. A layered structure advantageously permits layers to be in close proximity (eg a planar sensing waveguide and a planar inactive (reference) waveguide may be in close proximity to one another so as to minimise the deleterious effects of temperature and other environmental factors). Preferably the planar waveguide structure comprises a stack of transparent dielectric layers wherein layers are placed in close proximity. Preferably each layer is fabricated to allow equal amounts of electromagnetic radiation to propagate by simultaneous excitation of the guided modes in the structure.

Particularly preferably, the amount of electromagnetic radiation in the planar sensing waveguide/planar inactive waveguide or in the planar secondary waveguide/planar inactive secondary waveguide is equal.

The methods or process of the invention may be used to determine a qualitative characteristic of a chemical stimuli in an analyte which is introduced onto the planar waveguide structure. For example, a gaseous (eg vapour), liquid (eg solution) or solid phase analyte comprising chemical stimuli may be introduced onto the planar waveguide structure. Alternatively, a chemical reaction may take place which effects changes in the nature of the chemical stimuli in situ and causes a change in the localised environment.

The methods or process of the invention may be used to determine a qualitative characteristic of a physical stimulus such as inter alia pressure, position, temperature or vibration applied to the planar waveguide structure. The physical stimulus may be applied to the sensing layer or planar sensing waveguide of the planar waveguide structure via an impeller (for example) located on the sensing layer or planar sensing waveguide.

The methods or process of the invention may be used to determine a qualitative characteristic of a biological stimulus such as a protein.

The interaction of the stimulus with the planar sensing waveguide or sensing layer may be a binding interaction or absorbance or any other interaction.

Electromagnetic radiation generated from a conventional source may be propagated into the planar waveguide structure in a number of ways. In a preferred embodiment, electromagnetic radiation is simply input via an end face of the planar waveguide structure (this is sometimes described as "an end firing procedure"). Preferably (but not essentially), the electromagnetic radiation source provides incident electromagnetic radiation having a wavelength falling within the optical range. Propagating means may be employed for substantially simultaneously propagating incident electromagnetic radiation into a plurality of planar waveguides. For example, one or more coupling gratings or mirrors may be used. A tapered end coupler rather than a coupling grating or mirror may be used to propagate light into the lowermost planar waveguide.

The incident electromagnetic radiation may be oriented (eg plane polarised) as desired using an appropriate polarising means. The incident electromagnetic radiation may be focussed if desired using a lens or similar micro-focussing means.

Using electromagnetic radiation of different frequencies (either simultaneously or sequentially) varies the contributions of the various planar waveguides and may further enhance the utility of the planar waveguide structure.

As a consequence of the introduction of or changes in a physical, biological and/or chemical stimulus in the localised environment (ie a change in the refractive index of material in the localised environment), changes in the dielectric properties (eg the effective refractive index) of the planar sensing waveguide or sensing layer occur. This causes a measurable optical response (ie a change in the transmission of electromagnetic radiation down the planar sensing waveguide in whole waveguide mode or the planar secondary waveguide in evanescent field mode).

BRIEF DESCRIPTION OF THE DRAWINGS

The present invention will now be described in a non-limitative sense with reference to the accompanying Figures in which.

DETAILED DESCRIPTION

Figure 1:
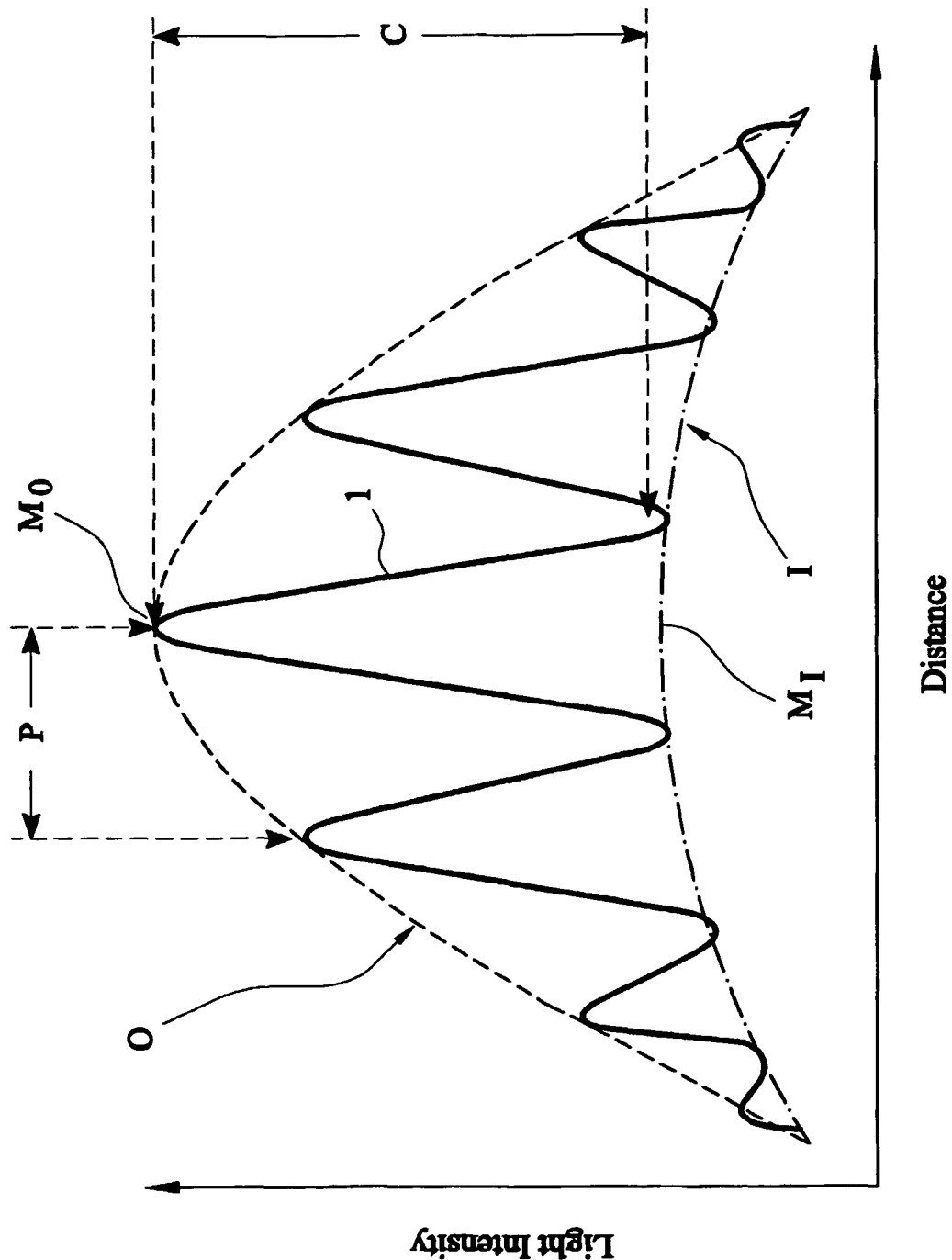
FIG. 1 illustrates various non-positional characteristics of interference fringes measured in accordance with embodiments of the methods and process of the invention.

FIG. 1 illustrates a typical pattern of interference fringes generated by a planar waveguide structure. Each fringe 1 is separated by the fringe period P and extends between an inner fringe envelope I and an outer fringe envelope O. The fringe contrast C represents the difference in intensity between the maxima ($M_O$) of the outer fringe envelope O and the maxima ($M_I$) of the inner fringe envelope I. The non-positional characteristics P and C may be used to deduce a qualitative characteristic of the planar waveguide structure or of a stimulus of interest to which it is exposed.

Figure 2A:
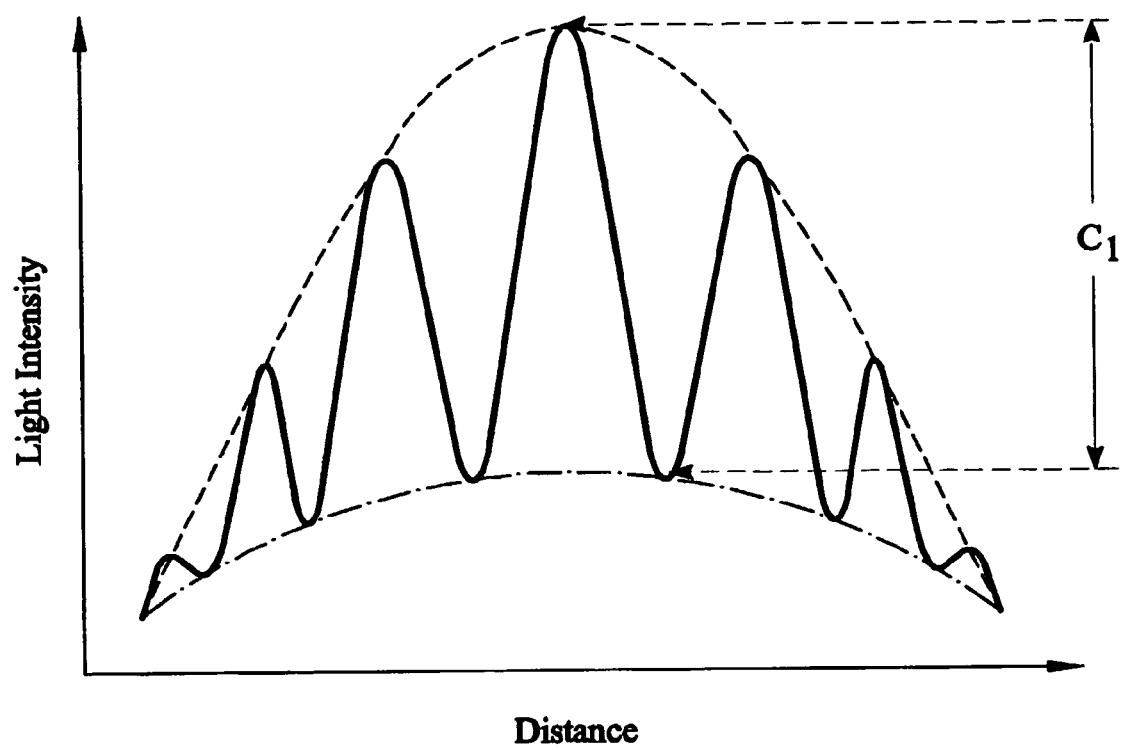
FIG. 2 illustrates the interference fringes measured in accordance with embodiments of the methods and process of the invention.
Figure 2B:
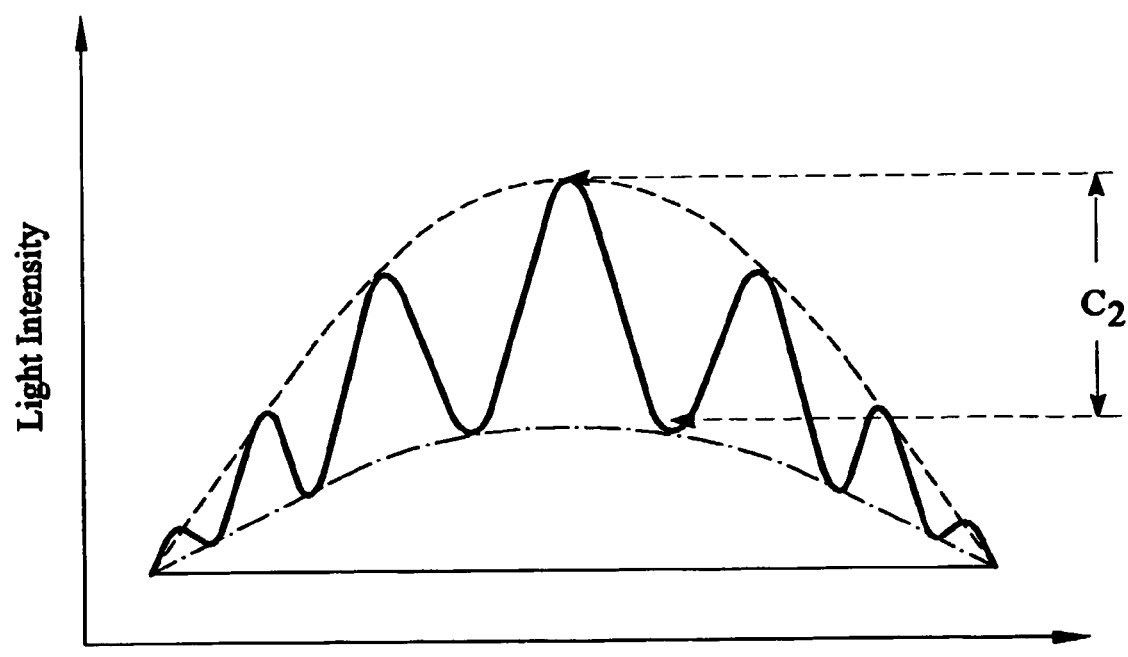
Figure 3A:
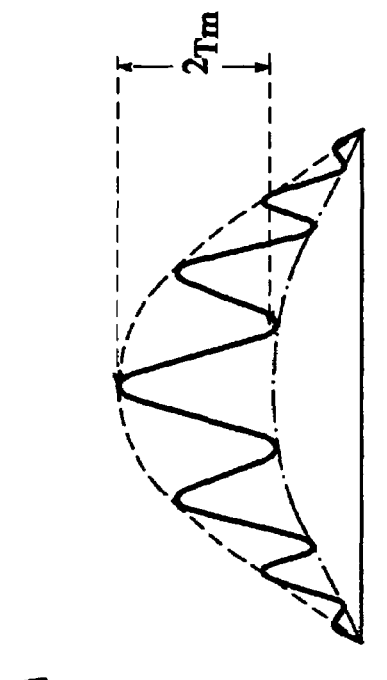
FIG. 3 illustrates the interference fringes measured in accordance with an embodiment of the process of the invention.
Figure 3B:
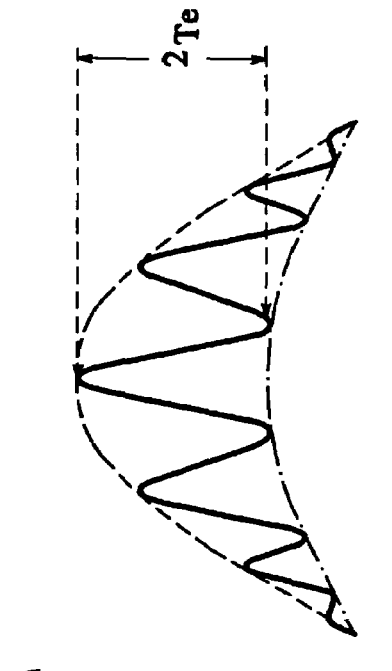
Figure 3C:
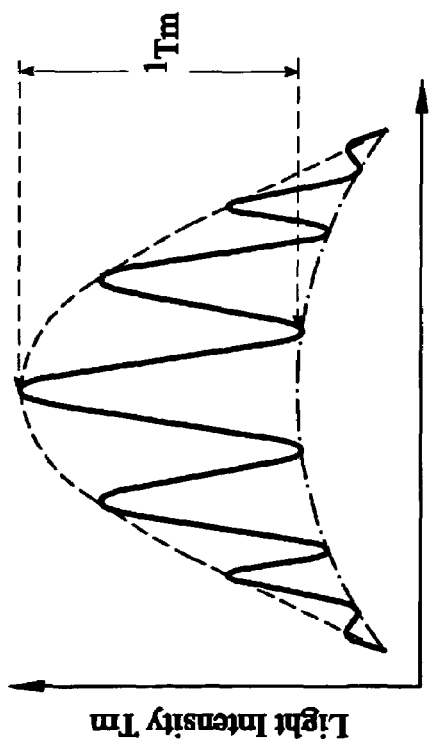
Figure 3D:
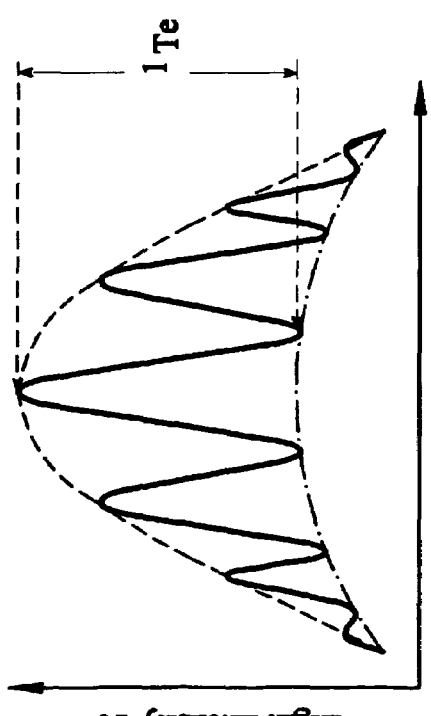

FIG. 2 illustrates the effect on the contrast of interference fringes of high scatter at the surface of the planar waveguide structure or of high radiation absorbtion by a stimulus of interest. Thus in accordance with an embodiment of the method of the invention, the contrast $C_1$ of the interference fringes in FIG. 2a may be related to a first planar waveguide structure which exhibits low surface scatter and the contrast $C_2$ of the interference fringes in FIG. 2b may be related to a second planar waveguide structure which exhibits high surface scatter. In accordance with an embodiment of the process of the invention, the contrast $C_1$ of the interference fringes in FIG. 2a may relate to a planar waveguide structure before it is exposed to a stimulus of interest and the contrast $C_2$ of the interference fringes in FIG. 2b may relate to the planar waveguide structure after exposure to a radiation absorbing chromophore.

FIG. 3 illustrates the pattern of interference fringes measured in accordance with an embodiment of the process of the invention. Firstly the planar waveguide structure is irradiated with electromagnetic radiation in TM mode to produce first interference fringes (FIG. 3a) and with electromagnetic radiation in TE mode to produce second interference fringes (FIG. 3c). The contrast $1_{TM}$ of the first interference fringes is measured and the contrast $1_{TE}$ of the second interference fringes is measured. Secondly the planar waveguide structure is exposed to a radiation absorbing stimulus. Thirdly the planar waveguide structure is irradiated with electromagnetic radiation in TM mode to produce third interference fringes (FIG. 3b) and with electromagnetic radiation in TE mode to produce fourth interference fringes (FIG. 3d). The contrast $2_{TM}$ of the third interference fringes is measured and the contrast $2_{TE}$ of the fourth interference fringes is measured. The distance of the radiation absorbing stimulus to the surface of the planar waveguide structure is proportional to $1_{TM}$-$2_{TM}/1_{TE}$-$2_{TE}$.

Figure 4B:
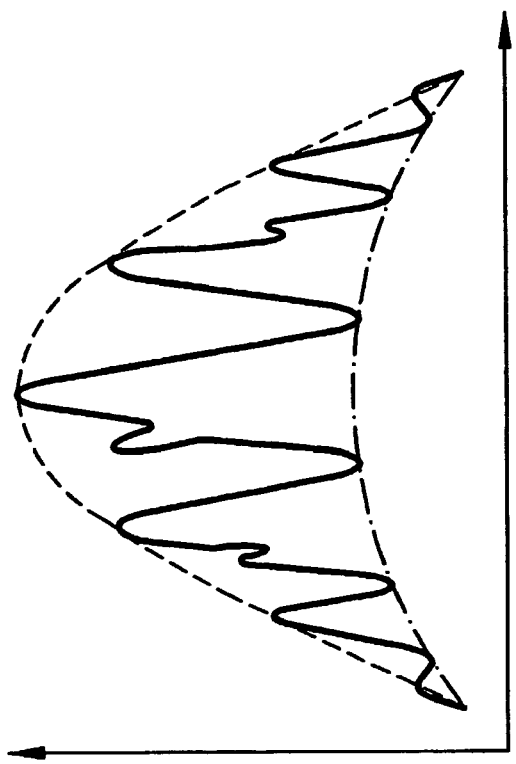
FIG. 4 illustrates the (a) calculated and (b) measured interference pattern of an embodiment of the method of the invention.
Figure 4A:
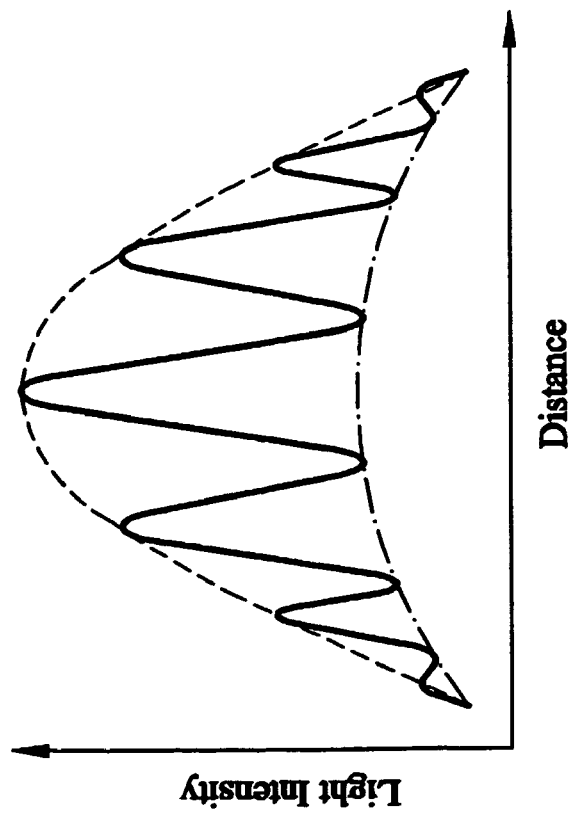

FIG. 4 illustrates the (a) calculated and (b) observed (measured) interference pattern of an embodiment of the method of the invention. The quality of the observed image may be quantified using standard statistical analysis to identify optical aberrations or to select a subset of high quality fringes for subsequent analytical measurements. A suitable equation for this purpose is set out in FIG. 4.

Figure 5A:
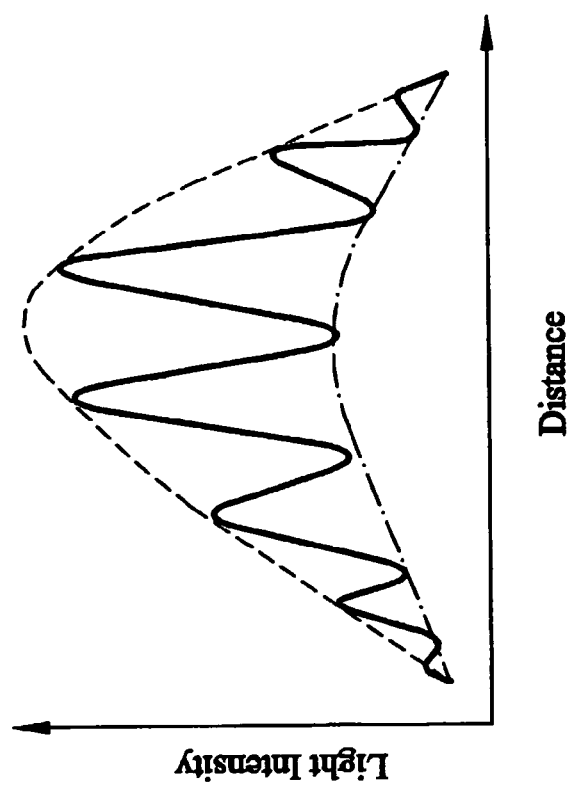
FIG. 5 illustrates the interference fringes measured in accordance with an embodiment of the method of the invention.
Figure 5B:
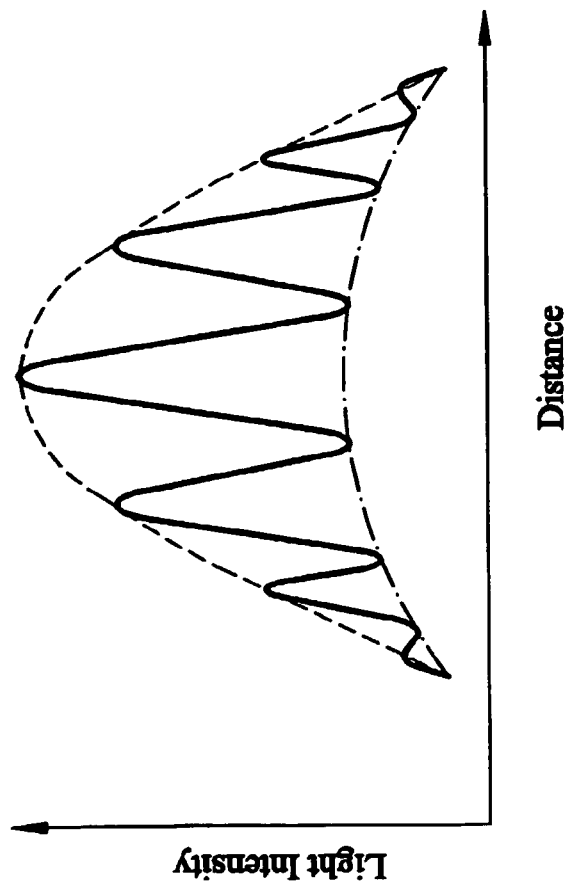

FIG. 5 illustrates the interference fringes measured in accordance with an embodiment of the method of the invention. The fringe envelope measured in FIG. 5a has been displaced from its origin and this may be related to lateral misalignment of the planar waveguide structure relative to a detector. The fringe envelope measured in FIG. 5b is distorted and this may be related to angular misalignment of the planar waveguide structure relative to a detector.

Figure 6:
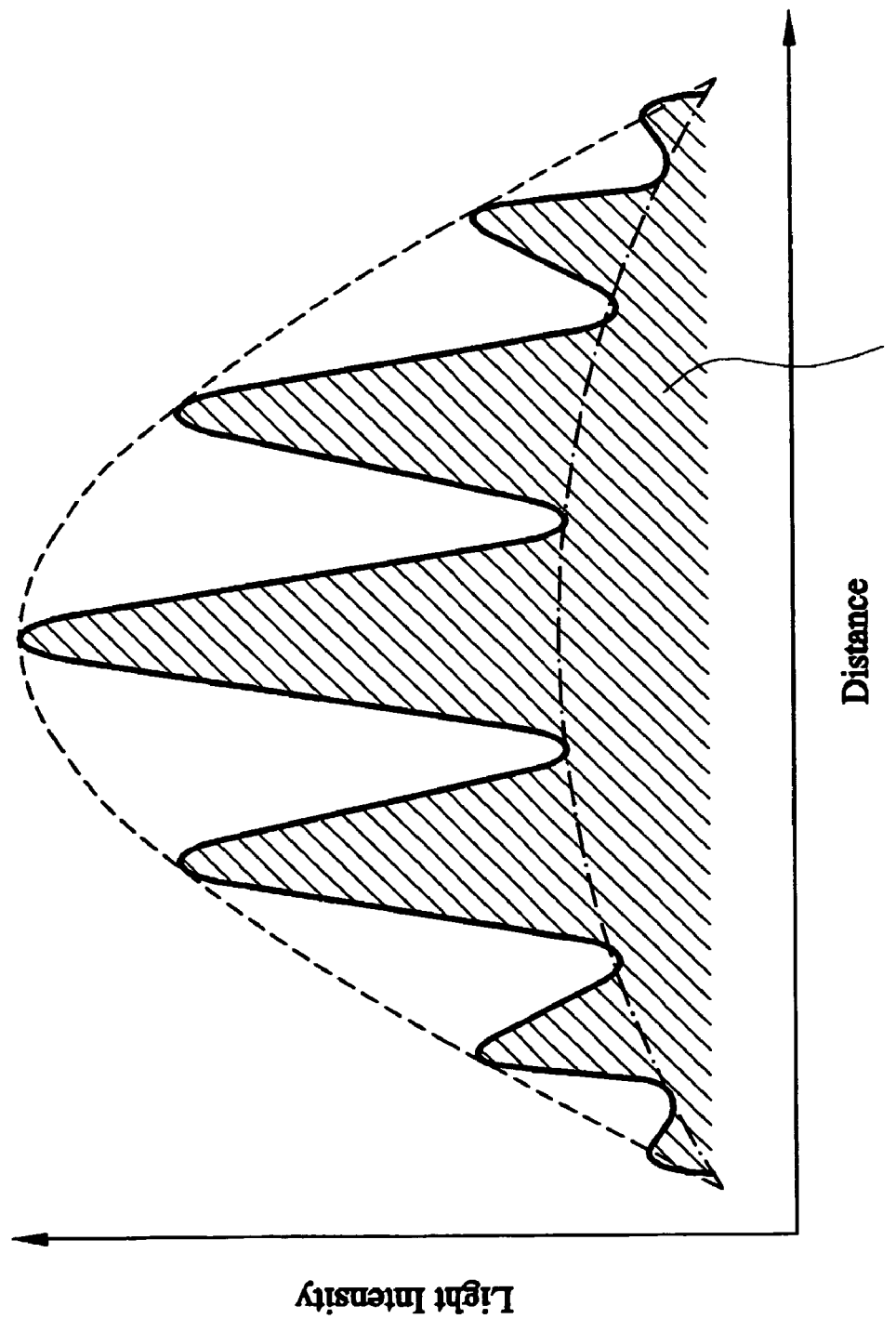
FIG. 6 illustrates the interference fringes measured in accordance with an embodiment of the method of the invention.

FIG. 6 illustrates the interference fringes measured in accordance with an embodiment of the method of the invention. The integral under the fringes I may be related to the power of the electromagnetic radiation passing through the planar waveguide structure. Changes in I may be attributed to scattering or absorbtion losses.

Figure 7A:
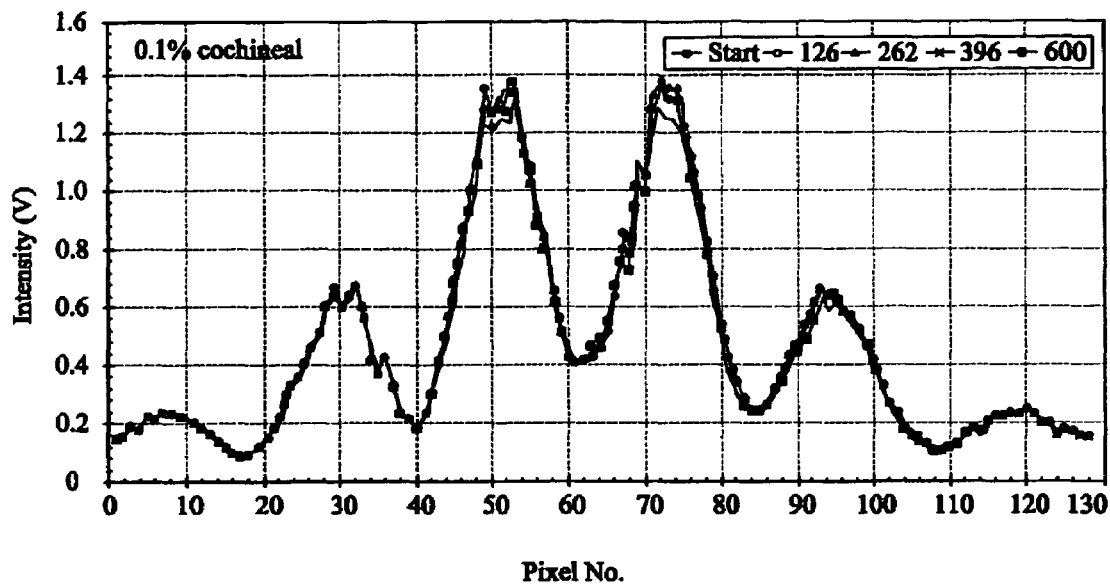
FIG. 7 illustrates the effect of various levels of cochineal (a red dye) on interference fringes.
Figure 7B:
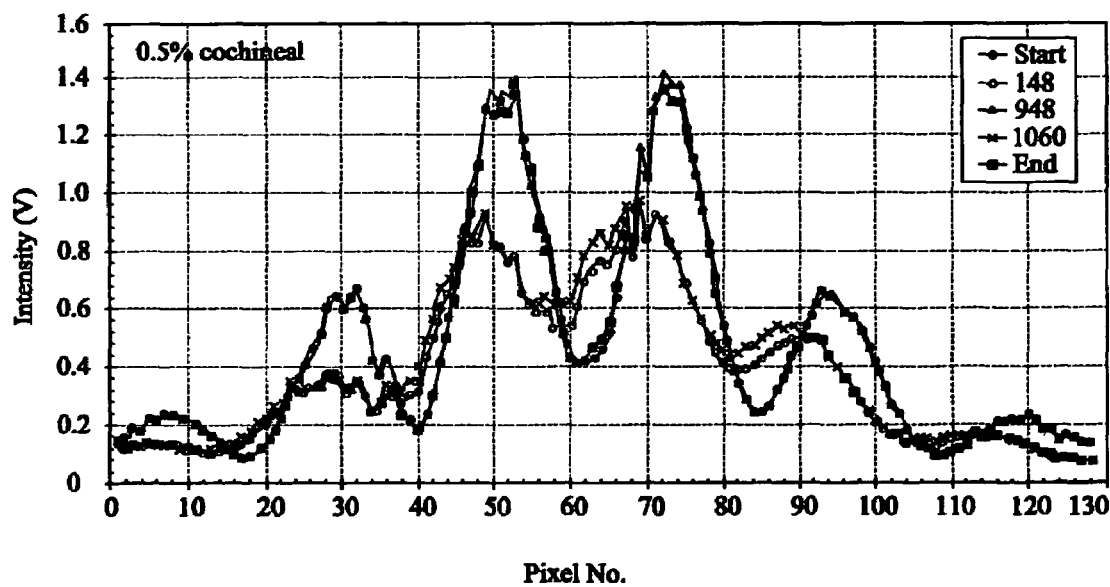

FIG. 7a illustrates the effect of cochineal (a red dye) on the interference fringes from a planar waveguide structure of the type disclosed in WO-A-98/22807 irradiated with a green laser (532 nm). The key indicates the times at which the fringes were measured. In FIG. 7(a), it will be seen that the concentration of cochineal of 0.1% is insufficient to substantially effect the interference fringes which therefore remain unchanged throughout the duration of the experiment. However it will be seen that on the introduction of 0.5% cochineal (FIG. 7b) at the start of the experiment, the contrast of the interference fringes is reduced significantly and that this effect is diminished over time as the effect of the cochineal is removed. This demonstrates how the contrast may be used to deduce the degree of absorbtion of a stimulus of interest.

The invention claimed is:

1. A process for determining a qualitative characteristic of a stimulus of interest in a localised environment, the process comprising:
  (A) providing an interferometric component capable of exhibiting a measurable response to a change in the localised environment caused by the introduction of or changes in the stimulus of interest;
  (B) introducing the stimulus of interest into the localised environment;
  (C1) irradiating the interferometric component with electromagnetic radiation of a first wavelength to generate first interference fringes;
  (C2) irradiating the interferometric component with electromagnetic radiation of a second wavelength to generate second interference fringes;
  (D1) measuring a non-positional characteristic of the first interference fringes;
  (D2) measuring a non-positional characteristic of the second interference fringes; and
  (E) determining the qualitative characteristic of the stimulus of interest in the localized environment from the non-positional characteristic of the first interference fringes and the non-positional characteristic of the second interference fringes.

2. A process as claimed in claim 1 wherein step (A) further comprises:
  (A1) irradiating the interferometric component with electromagnetic radiation of the first wavelength to generate first interference fringes;
  (A2) irradiating the interferometric component with electromagnetic radiation of the second wavelength to generate second interference fringes;
  (A3) measuring a non-positional characteristic of the first interference fringes;
  (A4) measuring a non-positional characteristic of the second interference fringes;
  and steps (C1), (C2), (D1), (D2) and (E) comprise:
  (C1) irradiating the interferometric component with electromagnetic radiation of the first wavelength to generate third interference fringes;
  (C2) irradiating the interferometric component with electromagnetic radiation of the second wavelength to generate fourth interference fringes;
  (D1) measuring a non-positional characteristic of the third interference fringes;
  (D2) measuring a non-positional characteristic of the fourth interference fringes;
  (E) determining the qualitative characteristic of the stimulus of interest in the localized environment from the non-positional characteristic of the first, second, third and fourth interference fringes.

3. A process as claimed in claim 1 wherein the non-positional characteristic of the interference fringes is the amplitude.

4. A method for determining a qualitative characteristic of a stimulus of interest in a localised environment, said method comprising:
  (A) providing an interferometric component capable of exhibiting a measurable response to a change in the localised environment caused by the introduction of or changes in the stimulus of interest;
  (B) introducing the stimulus of interest into the localised environment;
  (C) irradiating the interferometric component with electromagnetic radiation in TE and TM mode to generate output electromagnetic radiation;
  (D) measuring a transfer of power between TE and TM modes; and
  (E) determining the qualitative characteristic of the stimulus of interest in the localised environment from the transfer of power between TE and TM modes.

5. A method as claimed in claim 4 wherein the interferometric component is a planar waveguide structure selected from the group consisting of:
  a) one or more sensing layers capable of inducing in a planar secondary waveguide a measurable response to a change in the localised environment caused by the introduction of or changes in the stimulus of interest and a planar inactive secondary waveguide in which the sensing layer is incapable of inducing a measurable response to a change in the localised environment caused by the introduction of or changes in the stimulus of interest, and
  (b) a planar sensing waveguide capable of exhibiting a measurable response to a change in the localised environment caused by the introduction of or changes in the stimulus of interest and a planar inactive waveguide substantially incapable of exhibiting a measurable response to a change in the localised environment caused by the introduction of or changes in the stimulus of interest.

6. A method as claimed in claim 4 wherein the qualitative characteristic is the degree of anisotropy of the stimulus of interest.

7. A process as claimed in claim 1 wherein the interferometric component is a planar waveguide structure selected from the group consisting of:
   a) one or more sensing layers capable of inducing in a planar secondary waveguide a measurable response to a change in the localised environment caused by the introduction of or changes in the stimulus of interest and a planar inactive secondary waveguide in which the sensing layer is incapable of inducing a measurable response to a change in the localised environment caused by the introduction of or changes in the stimulus of interest, and
   b) a planar sensing waveguide capable of exhibiting a measurable response to a change in the localised environment caused by the introduction of or changes in the stimulus of interest and a planar inactive waveguide substantially incapable of exhibiting a measurable response to a change in the localised environment caused by the introduction of or changes in the stimulus of interest.

* * * * *